United States Patent [19]

Aberkane et al.

[11] Patent Number: 5,415,794
[45] Date of Patent: May 16, 1995

[54] NEW SULFURED COMPOUNDS, THEIR PREPARATION AND THEIR USE AS ADDITIVES FOR LUBRICATING OILS

[75] Inventors: Ourida Aberkane, Fameck; Maurice Born, Nanterre; Jean Luc Mieloszynski, Montigny Les Metz; Daniel Paquer, Vandoeuvre; Guy Barc, Rueil Malmaison, all of France

[73] Assignee: Institut Francais du Petrole, Rueil-Malmaison, France

[21] Appl. No.: 240,588

[22] Filed: May 10, 1994

Related U.S. Application Data

[63] Continuation-in-part of Ser. No. 940,890, Oct. 28, 1992, Pat. No. 5,324,858.

[30] Foreign Application Priority Data

Dec. 28, 1990 [FR] France .................. 90 16438

[51] Int. Cl.⁶ ........................................ C10M 135/22
[52] U.S. Cl. ................................................ 252/45
[58] Field of Search ............... 252/45; C10M 135/02, C10M 135/04, 135/20, 135/22

[56] References Cited

U.S. PATENT DOCUMENTS

| | | | |
|---|---|---|---|
| 2,695,316 | 11/1954 | McBride | 252/45 |
| 2,708,199 | 5/1955 | Eby | 252/45 |
| 3,471,404 | 10/1969 | Myers | 252/45 |
| 4,563,302 | 1/1986 | Griffin et al. | 252/45 |
| 4,645,610 | 2/1987 | Born et al. | 252/45 |
| 4,795,576 | 1/1989 | Born et al. | 252/45 |
| 5,051,198 | 9/1991 | Salomon | 252/47 |
| 5,324,858 | 6/1994 | Aberkane et al. | 568/21 |

FOREIGN PATENT DOCUMENTS

517542 10/1955 Canada .
2000130 1/1979 United Kingdom .

OTHER PUBLICATIONS

Miyazaki et al., Chem. Abstracts, 117(4)28349d (1990).

*Primary Examiner*—Prince Willis, Jr.
*Assistant Examiner*—Cephia D. Toomer
*Attorney, Agent, or Firm*—Millen, White, Zelano, & Branigan

[57] ABSTRACT

Novel sulfurized compounds, their preparation and use. The compounds are based on the general formula $$\{[R-S_x-(CH_2)_n-]_z CH_{3-z}-(CH_2)_p-\}_2 S_y,$$

in which R is a monovalent hydrocarbon radical having 1 to 30 carbon atoms, optionally functionalized; x is a number equal to or greater than 1; z is an integer equal to 1 or 2; when z=1, n is an integer from 0 to 3 and p is an integer from 0 to 3, with n+p being an integer from 0 to 3; when z=2, n is an integer from 1 to 3 and p is an integer from 0 to 3; and y is a number equal to or greater than 1, at least one of the numbers x and y being strictly greater than 1. The sulphurized compounds can be used as extreme pressure or wear prevention additives in lubricating oils, in particular in oils for gear systems and those used in working metal.

8 Claims, No Drawings

NEW SULFURED COMPOUNDS, THEIR PREPARATION AND THEIR USE AS ADDITIVES FOR LUBRICATING OILS

CROSS-REFERENCE TO RELATED APPLICATION

This application is a continuation-in-part of U.S. Ser. No. 07/940,890, filed Oct. 28, 1992, now U.S. Pat. No 5,324,858, which is the corresponding U.S. national phase application of international application PCT/FR91/01026, the entire disclosures of both of which are hereby incorporated by reference.

This invention relates to new sulfurized compounds, their preparation and their use as oil additives, in particular as anti-wear and extreme-pressure additives for lubricating oils.

The use of anti-wear and extreme-pressure additives, in particular in motor oils, transmission fluids, hydraulic fluids has been practiced for several decades. Many types of additives thus have been developed and several of them have made it possible to reduce very appreciably the deterioration of mechanisms and have thereby made it possible to extend their life.

Of the many anti-wear and extreme-pressure additives that have been studied, the dialkyl- and diaryldithiophosphates and the metal dialkyldithiocarbamates (those of zinc in particular), the alkylthiophosphates, tricresylphosphate, didodecylphosphate, the sulfured terpenes, the sulfurous spermaceti oil and various chlorinated compounds have proven to be most active and have undergone significant industrial development. Some of them are described in patents U.S. Pat. Nos. 2,364,283, 2,364,284, 2,365,938, 2,410,650, 2,438,876 and 3,190,833. Generally involved are compounds containing heteroatoms such as sulfur and phosphorus either alone (for example, tricresylphosphate, the sulfurous terpenes, the dithiocarbamates), or in combination (for example, metal dialkyldithiophosphates, alkylthiophosphates).

Of the sulfurous compounds, some can contain chemical functions imparting to the compound, in its use of additive, physico-chemical properties or improved mechanical performances. They involve, among others, phenol, nitrile, sulfoxide, xanthate functions, etc. In this connection, it is possible to cite U.S. Pat. Nos. 3,434,852, 3,984,336 and 3,994,923.

The amount of sulfur contained in the molecule of these sulfurous compounds is generally set by the stoichiometry of the reactions used during their synthesis, which imparts to them anti-wear and extreme-pressure properties on which it is not possible to perform any modification.

Now, new sulfurous compounds, usable as additives for lubricants, for which it is possible to modify the proportion of sulfur that they contain in their molecule and therefore to modulate at will their anti-wear and extreme-pressure properties, have been discovered.

The sulfured compounds of the invention can be defined by the fact that they correspond to the general formula:

$$\{[R-S_x-(CH_2)_n-)_n-]_z CH_{3-z}-(CH_2)_p-\}_2 S_y \quad (I)$$

in which R represents a monovalent hydrocarbonic radical with 1 to 30 carbon atoms, optionally functionalized; x is a number equal to or greater than 1; z is an integer equal to 1 or 2; when z=1, n is an integer from 0 to 3 and p is an integer from 0 to 3, with n+p being an integer from 0 to 3; when z=2, n is an integer from 1 to 3 and p is an integer from 0 to 3; and y is a number equal to or greater than 1, at least one of the numbers x and y being strictly greater than 1.

By functionalized radical is meant, for the definition of R, a radical comprising at least one hanging monovalent heteroatom, such as, for example, at least one chlorine atom, and/or at least one divalent heteroatom in the hydrocarbon chain, such as, for example, at least one atom of oxygen or sulfur, and/or at least one chemical function such as carboxylic acid, aldehyde, ketone, nitrile, hydroxyl or epoxide.

Further, it should be understood that the compounds of the invention can consist of mixtures of several molecules corresponding to formula (I) in which the value of x and the value of y will be different from one molecule to the next. Thus, it is possible to consider that in formula (I), numbers x and y represent statistical values.

In formula (I) of the sulfured compounds of the invention, more particularly R represents an alkyl radical containing, for example, 1 to 10 carbon atoms, or an alkenyl radical containing, for example, 2 to 10 carbon atoms, for example, a tert-butyl $(CH_3)_3C-$ radical or a methallyl radical $CH_2=C(CH_3)-CH_2-$; x has an average value of 1 to 3; z=1, with n+p from 1 to 3, and y has an average value of 1 to 3.

As examples of such sulfured compounds according to the invention, it is possible to cite the compounds of formulas:

[t.Bu—S—$(CH_2)_2$—]$_2$ S$_2$;
[t.Bu—S—$(CH_2)_3$—]$_2$ S$_2$;
[t.Bu—S—$(CH_2)_2$—]$_2$ S$_3$;
[t.Bu—S—$(CH_2)_3$—]$_2$ S$_3$;
[t.Bu—S$_2$—$(CH_2)_2$—]$_2$ S;
[t.Bu—S$_2$—$(CH_2)_3$—]$_2$ S;
[t.Bu—S$_2$—$(CH_2)_2$—]$_2$ S$_2$;
[t.Bu—S$_2$—$(CH_2)_3$—]$_2$ S$_2$;
[t.Bu—S$_2$—$(CH_2)_2$—]$_2$ S$_3$;
[t.Bu—S$_2$—$(CH_2)_3$—]$_2$ S$_3$;
[t.Bu—S$_3$—$(CH_2)_2$—]$_2$ S;
[t.Bu—S$_3$—$(CH_2)_3$—]$_2$ S;
[t.Bu—S$_3$—$(CH_2)_2$—]$_2$ S$_2$;
[t.Bu—S$_3$—$(CH_2)_3$—]$_2$ S$_2$;
[t.Bu—S$_3$—$(CH_2)_2$—]$_2$ S$_3$;
[t.Bu—S$_3$—$(CH_2)_3$—]$_2$ S$_3$;
[methallyl—S—$(CH_2)_2$—]$_2$ S$_2$;
[methallyl—S—$(CH_2)_3$—]$_2$ S$_2$;
[methallyl—S—$(CH_2)_2$—]$_2$ S$_3$;
[methallyl—S—$(CH_2)_3$—]$_2$ S$_3$;
[methallyl—S$_2$—$(CH_2)_2$—]$_2$ S;
[methallyl—S$_2$—$(CH_2)_3$—]$_2$ S;
[methallyl—S$_2$—$(CH_2)_2$—]$_2$ S$_2$;
[methallyl—S$_2$—$(CH_2)_3$—]$_2$ S$_2$;
[methallyl—S$_2$—$(CH_2)_2$—]$_2$ S$_3$;
[methallyl—S$_2$—$(CH_2)_3$—]$_2$ S$_3$;
[methallyl—S$_3$—$(CH_2)_2$—]$_2$ S;
[methallyl—S$_3$—$(CH_2)_3$—]$_2$ S;
[methallyl—S$_3$—$(CH_2)_2$—]$_2$ S$_2$;
[methallyl—S$_3$—$(CH_2)_3$—]$_2$ S$_2$;
[methallyl—S$_3$—$(CH_2)_2$—]$_2$ S$_3$;
and
[methallyl—S$_3$—$(CH_2)_3$—]$_2$ S$_3$.

It is also possible to consider more particularly the compounds corresponding to general formula (I) in which R represents an alkyl radical containing, for example, 1 to 10 carbon atoms or an alkenyl radical containing, for example, 2 to 10 carbon atoms, more particularly a tert-butyl or methallyl radical; x has an average value of 1 to 3, z is equal to 2 with n = 1 and p=0, and y has an average value of 1 to 3.

As examples of such compounds according to the invention, it is possible to cite those which correspond to the following formulas:

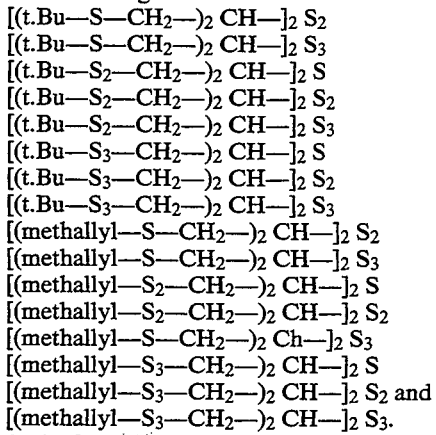

In the formulas above, t.Bu designates, in abbreviated form, the tert-butyl radical.

The sulfured compounds of the invention can be prepared by processes as illustrated in the examples that will be found below.

The sulfured compounds of the invention generally have a fairly high sulfur content, which varies according to the number of sulfur atoms of chains $-S_x-$ and $-S_y-$ present in their molecule. The sulfur content can be, for example, 20 to 45% by weight.

These compounds exhibit good anti-wear and extreme-pressure properties and can advantageously be used as additives for lubricating oils (mineral and/or synthetic), in particular oils for gear systems and those intended for working metals. The proportion of sulfured compound in the oil can be, for example, 0.05 to 20% by weight, more particularly 0.2 to 5% by weight.

The following examples illustrate the invention. Example 1 is given by way of comparison.

EXAMPLE 1: (comparative)

Synthesis of the compound

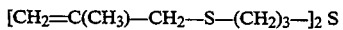

First Stage

Synthesis of methyl-2 propene-1 thiol-3

125.7 g (1.65 mole-g) of thiourea is dissolved in 250 cm³ of triethylene glycol brought to 75° C., then 135.75 g (1.5 mole-g) of methallyl chloride is gradually added, while keeping the reaction temperature less than 130° C. Then, 283.5 g (1.5 mole-g) of tetraethylene pentamine is gradually added, the thiol formed which distills (boiling point=40° C.) is collected and kept.

Second Stage

Synthesis of the corresponding monosulfured ethylene alcohol:

9.6 g (0.24 mole-g) of pure NaOH is dissolved in 200 cm³ of ethyl alcohol, then, after dissolution, 21.1 g (0.24 mole-g) of the thiol prepared in the first stage is added slowly, while keeping the reaction temperature below 40° C.; then, the mixture is brought to 50° C., this temperature is maintained for 0.5 hour, then it is cooled to 20° C.

18.9 g (0.2 mole-g) of chloro-3-propanol-1 is added, then the mixture is brought to the temperature of the reflux, this temperature is maintained for 6 hours, it is cooled and it is filtered to eliminate the NaCl formed.

The filtered alcoholic solution is diluted with 1000 cm³ of water, the sulfurous alcohol is extracted with benzene and washed with water; the organic solution recovered is dried on anhydrous $Na_2SO_4$, filtered, then evaporated under reduced pressure. The unsaturated sulfurous alcohol obtained (24 g) corresponds to the following analytical characteristics:

| C % by mass | | H % by mass | | S % by mass | |
|---|---|---|---|---|---|
| Found | Theory | Found | Theory | Found | Theory |
| 57.81 | 57.51 | 9.74 | 9.58 | 22.12 | 21.95 |

The infrared and RMN $^{13}C$ analyses confirm the chemical structure of the expected product:

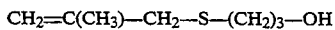

Third Stage

Synthesis of the chlorinated derivative corresponding to the sulfurous ethylene alcohol:

20 g (0.137 mole-g) of sulfurous ethylene alcohol obtained in the second stage is dissolved in 200 cm³ of chloroform; 8.16 g (0.685 mole-g) of $SOCl_2$ is then slowly added, then the mixture is brought to the temperature of the reflux; the same amount of $SOCl_2$ is again added, then it is allowed to boil for two hours.

After cooling, the solvent is eliminated by evaporation under reduced pressure; 22.2 g of product corresponding to the following analytical characteristics is collected:

| C % by mass | | H % by mass | | S % by mass | | Cl % by mass | |
|---|---|---|---|---|---|---|---|
| Found | Theory | Found | Theory | Found | Theory | Found | Theory |
| 50.81 | 51.04 | 7.98 | 7.90 | 19.31 | 19.48 | 21.94 | 21.57 |

The infrared and RMN $^{13}C$ analyses confirm the chemical structure of the expected product:

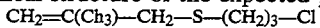

Fourth Stage

Synthesis of the monosulfured derivative corresponding to the preceding chlorinated monosulfured ethylene derivative:

19.3 g (0.08 mole-g) of $Na_2S$, 9 $H_2O$ is dissolved in 100 cm³ of ethyl alcohol; the solution obtained is brought to 40° C., then 20 g (0.121 mole-g) of the preceding chlorinated derivative dissolved in 25 cm³ of ethyl alcohol is slowly added. The mixture is brought to the temperature of the reflux and is kept at this temperature for 4 hours.

After cooling, the mixture is filtered to eliminate the NaCl formed, diluted with 500 cm³ of water and extracted in benzene; the recovered organic phase is dried on anhydrous $Na_2SO_4$, filtered, then evaporated under reduced pressure; the recovered product (17 g) corresponds to the following analytical characteristics:

| C % by mass | | H % by mass | | S % by mass | |
| --- | --- | --- | --- | --- | --- |
| Found | Theory | Found | Theory | Found | Theory |
| 58.01 | 57.90 | 9.08 | 8.96 | 32.87 | 33.15 |

The infrared and RMN $^{13}$C analyses confirm the chemical structure of the expected product:

[CH$_2$=C(CH$_3$)—CH$_2$—S—(CH$_2$)$_3$—]$_2$ S

EXAMPLE 2

Synthesis of the compound:

[CH$_2$=C(CH$_3$)—CH$_2$—S$_2$—(CH$_2$)$_3$—]$_2$ S

The experiment of example 1 is resumed at the level of the second stage for the preparation of a disulfured (statistical) ethylene alcohol, by operating under the following conditions:

9.6 g (0.24 mole-g) of pure NaOH is dissolved in 200 cm$^3$ of ethyl alcohol, then, after dissolution, 21.1 g (0.24 mole-g) of the thiol prepared in the first stage of example 1 is slowly added, while keeping the reaction temperature below 40° C.; 7.7 g (0.24 atom-g) of elementary sulfur then is added to form the statistical disulfide, then the mixture is brought to 50° C., this temperature is maintained for 0.5 hour, then it is cooled to 20° C.

The third and fourth stages of the experiment of example 1 are then continued, with the same operating conditions and with the same molar proportions of reagents, to obtain 24 g of a product having the following analytical characteristics:

| C % by mass | | H % by mass | | S % by mass | |
| --- | --- | --- | --- | --- | --- |
| Found | Theory | Found | Theory | Found | Theory |
| 47.87 | 47.41 | 7.54 | 7.34 | 44.79 | 45.19 |

The infrared and RMN $^{13}$C analyses confirm the chemical structure of the expected product:

[CH$_2$=C(CH$_3$)—CH$_2$—S$_2$—(CH$_2$)$_3$—]$_2$ S

EXAMPLE 3

Synthesis of the compound:

[CH$_2$=C(CH$_3$)—CH$_2$—S—(CH$_2$)$_3$—]$_2$ S$_2$

The experiment of example 1 is resumed at the level of the fourth stage for the preparation of a disulfide (statistical) of sodium, by operating under the following conditions:

19.3 g (0.08 mole-g) of Na$_2$S, 9 H$_2$O is dissolved in 100 cm$^3$ of ethyl alcohol; the solution obtained is brought to 40° C. then 2.66 g (0.08 atom-g) of elementary sulfur is added: the sodium disulfide is allowed to form for 0.5 hour at this same temperature, then the same amount of chlorinated derivative prepared as indicated in the third stage of example 1 is added: 20 g (0.121 mole-g) in 25 cm$^3$ of ethyl alcohol. The mixture is brought to the temperature of the reflux and is kept at this temperature for 4 hours.

After cooling, the mixture is filtered to eliminate the NaCl formed, diluted with 500 cm$^3$ of water and extracted in benzene; the recovered organic phase is dried on anhydrous Na$_2$SO$_4$, filtered, then evaporated under reduced pressure; the recovered product (20.3 g) has the following analytical characteristics:

| C % by mass | | H % by mass | | S % by mass | |
| --- | --- | --- | --- | --- | --- |
| Found | Theory | Found | Theory | Found | Theory |
| 52.48 | 52.13 | 8.34 | 8.07 | 39.12 | 39.80 |

The infrared and RMN $^{13}$C analyses confirm the chemical structure of the expected product:

[CH$_2$=C(CH$_3$)—CH$_2$—S—(CH$_2$)$_3$—]$_2$ S$_2$

EXAMPLE 4

Evaluation of the extreme-pressure and anti-wear properties of the additives of examples 1 to 3.

Tests showing the extreme-pressure and anti-wear properties of the additives of examples 1 to 3 have been performed with a 4-ball machine according to the procedure of ASTM D 2783-82 with concentrations such that the sulfur content of mineral oil SAE 90 is equal to 0.4% by mass.

It is found, in view of these results, that the additives of examples 2 and 3 have improved anti-wear and extreme-pressure properties, with equal sulfur concentration, relative to that of the additive of comparative example 1.

EXAMPLE 5

Synthesis of the compound (t.Bu—S—(CH$_2$)$_3$—)$_2$ S$_2$

First Stage

Synthesis of the corresponding sulfurous alcohol t.Bu—S—(CH$_2$)$_3$—OH 100 g (2.5 mole-g) of soda is dissolved in 1250 cm$^3$ of anhydrous methyl alcohol, then, after dissolution, 180.0 g (2.0 mole-g) of 2-methyl-2-propanethiol (tert-butyl mercaptan) is added slowly while keeping the reaction temperature below 40° C. The mixture is then brought to 50° C. and this temperature is maintained for 0.5 hour, then it is cooled to 20° C.

189.0 g (2.0 mole-g) of 3-chloro-1 propanol is added, then the mixture is brought to the temperature of the reflux, this temperature is maintained for 6 hours, it is cooled and it is filtered to eliminate the NaCl formed.

The collected filtered alcoholic solution is diluted with 7500 cm$^3$ of water, the sulfurous alcohol is extracted with dichloromethane and washed with water; the recovered organic solution is dried on anhydrous Na$_2$SO$_4$, filtered, then evaporated under reduced pressure to obtain sulfurous alcohol (290.0 g) whose analytical characteristics are the following:

| C % by mass | | H % by mass | | S % by mass | |
| --- | --- | --- | --- | --- | --- |
| Found | Theory | Found | Theory | Found | Theory |
| 56.92 | 56.71 | 10.94 | 10.88 | 21.35 | 21.63 |

The infrared and RMN $^{13}$C analyses confirm the chemical structure of the expected product.

Second Stage

Synthesis of the chlorinated derivative corresponding to the sulfurous alcohol t.Bu—S—(CH$_2$)$_3$—Cl 240 g (0.8 mole-g) of the sulfurous alcohol obtained in the first stage is dissolved in 1250 cm$^3$ of chloroform;

49.2 g (0.41 mole-g) of SOCl₂ is then slowly added, then the mixture is refluxed; the same amount of SOCl₂ is added again, then it is allowed to boil for two hours.

After cooling, washing with water and drying on anhydrous Na₂SO₄, the solvent is eliminated by evaporation under reduced pressure; 130 g of product is collected corresponding to the following analytical characteristics:

| C % by mass | | H % by mass | | S % by mass | | Cl % by mass | |
|---|---|---|---|---|---|---|---|
| Found | Theory | Found | Theory | Found | Theory | Found | Theory |
| 50.67 | 50.43 | 9.17 | 9.07 | 19.10 | 19.23 | 21.12 | 21.27 |

The infrared and RMN $^{13}$C analyses confirm the chemical structure of the expected product.

Third Stage

Synthesis of said polysulfurous compound 6.6 g (0.165 mole-g) of soda is dissolved in 100 cm³ of absolute methyl alcohol, then, after dissolution, 2.83 g (0.083 mole-g) of gaseous H₂S is slowly introduced. Then, 2.66 g (0.083 at-g) of sublimed sulfur is added to form the statistical sodium disulfide; the obtained mixture is brought to 40° C. then 25 g (0.15 mole-g) of the halogenated derivative obtained at the end of the second stage is slowly added; the mixture is brought to the temperature of the reflux and it is allowed to react for 4 hours. After cooling, the mixture is filtered to eliminate the NaCl formed, diluted with 1 l of water extracted in chloroform, dried on Na₂SO₄, filtered, then evaporated under reduced pressure.

23.0 g of product thus is collected whose analytical characteristics are the following:

| C % by mass | | H % by mass | | S % by mass | |
|---|---|---|---|---|---|
| Found | Theory | Found | Theory | Found | Theory |
| 52.12 | 51.48 | 9.43 | 9.26 | 38.50 | 39.26 |

The infrared and RMN $^{13}$C analyses confirm the expected statistical disulfide chemical structure:

(t.Bu—S—(CH₂)₃—)₂ S₂

EXAMPLE 6

Synthesis of the compound (t.Bu—S—(CH₂)₃—)₂ S₃

The third stage of example 5 is resumed by using, this time, 5.32 g (0.166 mole-g) of elementary sulfur to form the intended statistical trisulfide; after reaction with 25 g of the halogenated derivative obtained in the second stage of this same example and after continuation of the operating mode, 25.5 g of product is collected whose analytical characteristics are the following:

| C % by mass | | H % by mass | | S % by mass | |
|---|---|---|---|---|---|
| Found | Theory | Found | Theory | Found | Theory |
| 47.01 | 46.87 | 8.75 | 8.43 | 44.14 | 44.69 |

The infrared and RMN $^{13}$C analyses confirm the expected statistical trisulfide chemical structure.

EXAMPLE 7

Synthesis of the compound

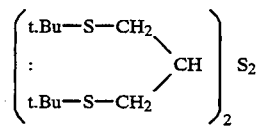

Synthesis of the corresponding sulfurous alcohol:

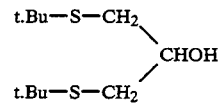

The first stage of example 5 is resumed by using 12 g (0.3 mole-g) of soda, 150 cm³ of methyl alcohol, 27 g (0.3 mole-g) of tert-butyl mercaptan and 12.9 g (0.1 mole-g) of 1,3-dichloro-2-propanol; after treatments, 22 g of sulfurous alcohol is recovered whose analytical characteristics are the following:

| C % by mass | | H % by mass | | S % by mass | |
|---|---|---|---|---|---|
| Found | Theory | Found | Theory | Found | Theory |
| 56.02 | 55.88 | 10.36 | 10.23 | 26.82 | 27.12 |

The infrared and RMN $^{13}$C analyses confirm the chemical structure of the expected product.

Synthesis of the halogenated derivative corresponding to the sulfurous alcohol

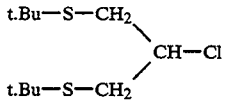

The second stage of example 5 is resumed by using 20 g (0.0846 mole-g) of the preceding sulfurous alcohol, 125 cm³ of chloroform, and 11.17 g (0.093 mole-g) of SOCl₂; after treatments, 19.5 g of product is recovered corresponding to the following characteristics:

| C % by mass | | H % by mass | | S % by mass | | Cl % by mass | |
|---|---|---|---|---|---|---|---|
| Found | Theory | Found | Theory | Found | Theory | Found | Theory |
| 52.04 | 51.83 | 9.27 | 9.09 | 24.95 | 25.16 | 13.67 | 13.91 |

The infrared and RMN $^{13}$C analyses confirm the chemical structure of the expected product.

Synthesis of said polysulfurous compound

The third stage of example 5 is resumed by using 3.3 g (0.0815 mole-g) of soda in 100 cm³ of methyl alcohol, 1.4 g (0.0425 mole-g) of H₂S, 1.36 g (0.0425 at-g) of sulfur and 19 g (0.0745 mole-g) of the preceding halogenated derivative; after reaction then treatments, 17 g of product corresponding to the following characteristics is recovered:

| C % by mass | | H % by mass | | S % by mass | |
|---|---|---|---|---|---|
| Found | Theory | Found | Theory | Found | Theory |
| 52.88 | 52.53 | 9.47 | 9.22 | 37.69 | 38.25 |

The infrared and RMN $^{13}$C analyses confirm the expected statistical disulfide chemical structure.

EXAMPLE 8

Synthesis of the compound (t.Bu—S—(CH$_2$)$_2$—)$_2$ S$_2$

The experiment of example 5 is resumed, with the same molar proportions of reagents and the same operating conditions, by using 2-chloroethanol; after reactions and treatment, a product corresponding to the following characteristics is recovered:

| C % by mass | | H % by mass | | S % by mass | |
|---|---|---|---|---|---|
| Found | Theory | Found | Theory | Found | Theory |
| 48.78 | 48.27 | 8.98 | 8.78 | 42.21 | 42.95 |

The infrared and RMN $^{13}$C analyses confirm the expected statistical disulfide chemical structure.

EXAMPLE 9

Synthesis of the compound (t.Bu—S$_2$—(CH$_2$)$_3$—)$_2$ S

First Stage

Synthesis of the corresponding sulfurous alcohol t.Bu—S$_2$—(CH$_2$)$_3$—OH

The experiment of example 5 is resumed by using, in the first stage, 16 g (0.4 mole-g) of soda in 250 cm$^3$ of methyl alcohol, 36 g (0.4 mole-g) of tert-butyl mercaptan and by adding 12.83 g (0.4 at-g) of sulfur to form the statistical alkaline disulfide.

The synthesis is continued by using 28.35 g (0.3 mole-g) of 3-chloro-1-propanol; after treatments, 50 g of product is collected.

Second Stage

Synthesis of the chlorinated derivative corresponding to the sulfurous alcohol t.Bu—S$_2$—(CH$_2$)$_3$—Cl Under the operating conditions of the second stage of example 5, 45 g (0.277 mole-g) of the preceding sulfurous alcohol is caused to react with 34 g of SOCl$_2$; after reaction and treatments, 51 g of chlorinated product is recovered.

Third Stage

Synthesis of said polysulfurous compound

Under the conditions indicated in example 5, 6.6 g (0.165 mole-g) of soda in 100 cm$^3$ of methyl alcohol is caused to react with 2.81 g (0.825 mole-g) of H$_2$S. 25 g (0.125 mole-g) of chlorinated product obtained above then is added; after treatments, 21 g of product whose characteristics are the following is collected:

| C % by mass | | H % by mass | | S % by mass | |
|---|---|---|---|---|---|
| Found | Theory | Found | Theory | Found | Theory |
| 47.53 | 46.87 | 8.94 | 8.43 | 43.53 | 44.69 |

The GPC, infrared and RMN $^{13}$C analyses confirm the expected statistical disulfide chemical structure, with impurities of the polysulfide type of di-tert-butyl in a very minor amount.

EXAMPLE 10

Synthesis of the compound (t.Bu—S$_2$—(CH$_2$)$_3$—)$_2$ S$_2$

The experiment of example 9 is resumed by adding, in the third stage, 2.41 g (0.075 at-g) of sulfur to form a statistical alkaline disulfide. After reaction with the chlorinated derivative (25 g—0.0125 mole-g) then treatments, 20 g of product corresponding to the following characteristics is collected:

| C % by mass | | H % by mass | | S % by mass | |
|---|---|---|---|---|---|
| Found | Theory | Found | Theory | Found | Theory |
| 43.84 | 43.03 | 7.89 | 7.74 | 48.32 | 49.23 |

The GPC, infrared and RMN $^{13}$C analyses confirm the expected statistical disulfide chemical structure, with impurities of the polysulfide type of di-tert-butyl in a very minor amount.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A composition comprising:

a lubricating oil and an extreme pressure or anti-wear additive wherein said additive is a polysulfide compound of the formula:

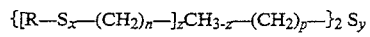

wherein

R is alkyl having 1–10 carbon atoms or alkenyl having 2–10 carbon atoms;

x is 2–3;

z is 1;

n+p is 1–3; and y is 1–3.

2. A composition according to claim 1, in which the concentration of said compound is 0.05 to 20% by weight relative to said lubricating oil.

3. A composition according to claim 1, wherein R is tertbutyl or methallyl.

4. A composition according to claim 3, wherein said compound is:

[t.Bu—S$_2$—(CH$_2$)$_2$—]$_2$ S;
[t.Bu—S$_2$—(CH$_2$)$_3$—]$_2$ S;
[t.Bu—S$_2$—(CH$_2$)$_2$—]$_2$ S$_2$;
[t.Bu—S$_2$—(CH$_2$)$_3$—]$_2$ S$_2$;
[t.Bu—S$_2$—(CH$_2$)$_2$—]$_2$ S$_3$;
[t.Bu—S$_2$—(CH$_2$)$_3$—]$_2$ S$_3$;
[t.Bu—S$_3$—(CH$_2$)$_2$—]$_2$ S;
[t.Bu—S$_3$—(CH$_2$)$_3$—]$_2$ S;
[t.Bu—S$_3$—(CH$_2$)$_2$—]$_2$ S$_2$;
[t.Bu—S$_3$—(CH$_2$)$_3$—]$_2$ S$_2$;
[t.Bu—S$_3$—(CH$_2$)$_2$—]$_2$ S$_3$;
[t.Bu—S$_3$—(CH$_2$)$_3$—]$_2$ S$_3$;
[methallyl—S$_2$—(CH$_2$)$_2$—]$_2$ S;
[methallyl—S$_2$—(CH$_2$)$_3$—]$_2$ S;
[methallyl—S$_2$—(CH$_2$)$_2$—]$_2$ S$_2$;
[methallyl—S$_2$—(CH$_2$)$_3$—]$_2$ S$_2$;
[methallyl—S$_2$—(CH$_2$)$_2$—]$_2$ S$_3$;
[methallyl—S$_2$—(CH$_2$)$_3$—]$_2$ S$_3$;
[methallyl—S$_3$—(CH$_2$)$_2$—]$_2$ S;
[methallyl—S$_3$—(CH$_2$)$_3$—]$_2$ S;
[methallyl—S$_3$—(CH$_2$)$_2$—]$_2$ S$_2$;
[methallyl—S$_3$—(CH$_2$)$_3$—]$_2$ S$_2$;
[methallyl—S$_3$—(CH$_2$)$_2$—]$_2$ S$_3$; or

[methallyl—S$_3$—(CH$_2$)$_3$—]$_2$ S$_3$.

5. A composition comprising:
a lubricating oil and an extreme pressure or anti-wear additive, wherein said additive is a polysulfide compound of the formula:

$$\{[R-S_x-(CH_2)_n-]_z CH_{3-z}-(CH_2)_p-\}_2 S_y$$

wherein
R is alkyl having 1–10 carbon atoms or alkenyl having 2–10 carbon atoms;
x is 1–3;
z is 2;
n is 1;
p is zero; and
y is 1–3,
wherein one of x and y is greater than 1.

6. A composition according to claim 5, wherein R is tert-butyl or methallyl.

7. A composition according to claim 6, wherein said compound is:
[(t.Bu—S—CH$_2$—)$_2$ CH—]$_2$ S$_2$;
[(t.Bu—S—CH$_2$—)$_2$ CH—]$_2$ S$_3$;
[(t.Bu—S$_2$—CH$_2$—)$_2$ CH—]$_2$ S;
[(t.Bu—S$_2$—CH$_2$—)$_2$ CH—]$_2$ S$_2$;
[(t.Bu—S$_2$—CH$_2$—)$_2$ CH—]$_2$ S$_3$;
[(t.Bu—S$_3$—CH$_2$—)$_2$ CH—]$_2$ S;
[(t.Bu—S$_3$—CH$_2$—)$_2$ CH—]$_2$ S$_2$;
[(t.Bu—S$_3$—CH$_2$—)$_2$ CH—]$_2$ S$_3$;
[(methallyl—S—CH$_2$—)$_2$ CH—]$_2$ S$_2$;
[(methallyl—S—CH$_2$—)$_2$ CH—]$_2$ S$_3$;
[(methallyl—S$_2$—CH$_2$—)$_2$ CH—]$_2$ S;
[(methallyl—S$_2$—CH$_2$—)$_2$ CH—]$_2$ S$_2$;
[(methallyl—S$_2$—CH$_2$—)$_2$ CH—]$_2$ S$_3$;
[(methallyl—S$_3$—CH$_2$—)$_2$ CH—]$_2$ S;
[(methallyl—S$_3$—CH$_2$—)$_2$ CH—]$_2$ S$_2$; or
[(methallyl—S$_3$—CH$_2$—)$_2$ CH—]$_2$ S$_3$.

8. A composition according to claim 5, in which the concentration of said compound is 0.05 to 20% by weight relative to said lubricating oil.

* * * * *